United States Patent [19]
Sato et al.

[11] Patent Number: 5,633,418
[45] Date of Patent: May 27, 1997

[54] METHOD FOR DIMERIZING AN OLEFIN

[75] Inventors: Keiichi Sato; Yuji Kawaragi; Yasuko Higashino, all of Yokohama, Japan

[73] Assignee: Mitsubishi Chemical Corporation, Tokyo, Japan

[21] Appl. No.: 502,888

[22] Filed: Jul. 17, 1995

[30] Foreign Application Priority Data

Jul. 18, 1994 [JP] Japan ................................... 6-165489

[51] Int. Cl.$^6$ .................... C07C 2/22; C07C 2/30
[52] U.S. Cl. ................ 585/513; 585/514; 585/509
[58] Field of Search ........................ 585/513, 514, 585/509, 510

[56] References Cited

U.S. PATENT DOCUMENTS

| | | |
|---|---|---|
| 4,599,206 | 7/1986 | Billig et al. ................ 558/85 |
| 5,414,160 | 5/1995 | Sato et al. ................ 568/883 |
| 5,446,213 | 8/1995 | Sato et al. ................ 568/883 |

*Primary Examiner*—Helane Myers
*Assistant Examiner*—Bekir L. Yildirim
*Attorney, Agent, or Firm*—Oblon, Spivak, McClelland, Maier & Neustadt, P.C.

[57] ABSTRACT

A method for dimerizing an olefin, which comprises dimerizing an olefin in the presence of a catalyst, wherein a nickel compound, an organic aluminum compound and a phosphite compound of the formula (I):

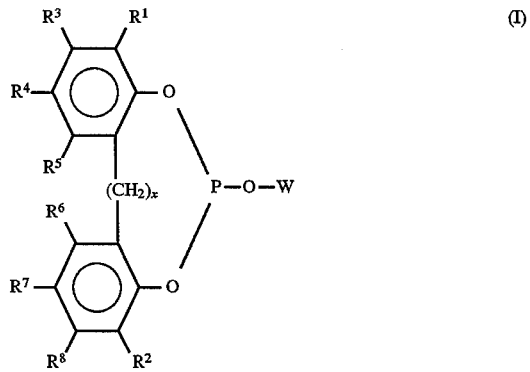

wherein each of $R^1$ and $R^2$ which may be the same or different, is a hydrocarbon group, each of $R^3$ to $R^8$ which may be the same or different, is a substituent containing no oxygen atom, or a hydrogen atom, W is a substituted or unsubstituted aromatic hydrocarbon group, and x is 0 or 1, are used as the catalyst.

11 Claims, No Drawings

METHOD FOR DIMERIZING AN OLEFIN

BACKGROUND OF THE INVENTION

1. Field of the Invention

The present invention relates to a method for dimerizing an olefin such as ethylene, propylene, butene, pentene, decene or tetradecene by means of a certain specific catalyst.

The dimerization product of an olefin produced by the dimerization method of the present invention may be hydroformylated, for example, by reacting it with carbon monoxide and hydrogen in the presence of e.g. a Group VIII metal catalyst such as a Rh catalyst, and the obtained aldehyde may further be hydrogenated to obtain an alcohol. Such an alcohol may be esterified with a carboxylic acid such as phthalic acid to obtain an industrially useful compound which can be used as a plasticizer for synthetic resins.

2. Discussion of Background

Many studies have been made with respect to a catalyst system by which a monoolefin such as ethylene, propylene, butene, pentene, decene or tetradecene is uniformly dimerized. As the catalyst system, a Ziegler type catalyst employing a transition metal as a principal catalyst component, is usually superior from the viewpoint of the selectivity for a dimer of a monoolefin. Especially when a catalyst obtained from a mixture of a nickel compound and an organic aluminum halide, is used, excellent results have been obtained with respect to both the dimerization activity and the selectivity.

Further, many studies have also been made with respect to a catalyst system wherein an organic phosphorus compound is used as a third catalyst component together with the above-mentioned catalyst components, and it is known that such a catalyst component is influential over the catalytic activity and the product selectivity. As catalyst systems wherein such organic phosphorus compounds are incorporated, ① Japanese Examined Patent Publication No. 34007/1971 discloses a catalyst system comprising a π-allyl type nickel complex, an organic aluminum halide and an organic phosphine, ② Japanese Examined Patent Publications No. 30241/1973 and 30041/1975 disclose catalyst systems comprising organic phosphine complexes of nickel represented by $(R_4P)^+(R_3PNiX_3)^-$ (wherein R is a hydrocarbyl group or hydrogen, and X is chlorine, bromine or iodine) and $NiX'_2 (PR'_3)_2$ (wherein X' is chlorine, bromine or iodine, and R' is an alkyl group), respectively, and ③ Japanese Unexamined Patent Publication No. 339174/1993 discloses a catalyst system wherein a halogenated phenol, water and a sulfonic acid are added as additives to a nickel compound, an alkylaluminum and a trivalent phosphorus compound, wherein the trivalent phosphorus compound may be not only the above-mentioned organic phosphine but also a trivalent organic phosphite compound such as triethyl phosphite, tri-t-butyl phosphite, triphenyl phosphite or tri-p-tolyl phosphite.

As described above, various organic phosphorus compounds have been proposed as catalyst components to be used for the dimerization reaction, but these compounds are not necessarily satisfactory for industrial operation. Namely, the catalyst system of the above ① is extremely unstable against air, hence its handling is troublesome, and it also has a drawback that synthesis of the catalyst is complex. Also, the catalyst systems of the above ② involve a difficulty for industrial operation, since it is required to separately prepare complicated nickel complexes. The catalyst system of the above ③ exhibits a high catalytic activity for dimerization of a lower α-olefin such as ethylene or propylene, but its dimerization activity is inadequate for an internal olefin, for example, a substrate such as 2-butene. Therefore, it is not satisfactory in the catalytic efficiency for a starting material substrate containing an internal olefin.

Thus, catalyst systems wherein various organic phosphorus compounds are used as co-catalysts, have been proposed as catalysts for dimerization reactions of olefins, but they are not necessarily satisfactory for industrial operation from the viewpoint of the stability of catalysts, the preparation method, the catalytic efficiency or the product selectivity and thus still have problems to be solved.

SUMMARY OF THE INVENTION

Accordingly, it is an object of the present invention to develop a catalyst system for the dimerization reaction excellent in the catalytic efficiency and the selectivity for the desired product.

The present inventors have conducted extensive studies to solve the above-mentioned problems in the method for dimerizing olefins and as a result, have found that a certain specific dimerization catalyst is capable of promoting the reaction with an extremely high activity while increasing the selectivity for the dimerization product. The present invention has been accomplished on the basis of this discovery.

Namely, the present invention provides a method for dimerizing an olefin, which comprises dimerizing an olefin in the presence of a catalyst, wherein a nickel compound, an organic aluminum compound and a phosphite compound of the formula (I):

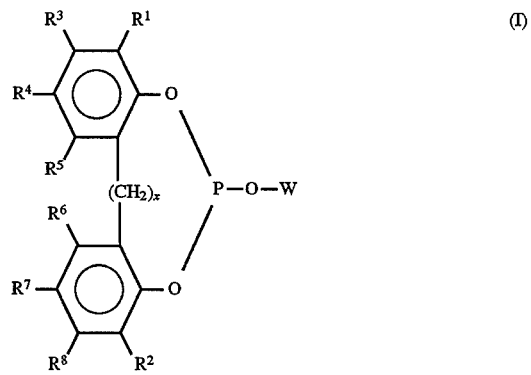

wherein each of $R^1$ and $R^2$ which may be the same or different, is a hydrocarbon group, each of $R^3$ to $R^8$ which may be the same or different, is a substituent containing no oxygen atom, or a hydrogen atom, W is a substituted or unsubstituted aromatic hydrocarbon group, and x is 0 or 1, are used as the catalyst.

DETAILED DESCRIPTION OF THE PREFERRED EMBODIMENTS

Now, the present invention will be described in detail.

The olefin to be used in the dimerization method of the present invention includes, for example, ethylene, propylene, butenes, pentenes, hexenes, decenes and tetradecenes, and it may be a mixture thereof. As mentioned above, the formed olefin obtained by the dimerization method of the present invention can be converted to an alcohol by hydroformylation and hydrogenation, and this alcohol can be further esterified for use as a plasticizer. When an application to such an alcohol for a plasticizer is taken into consideration, the starting material olefin is preferably a single product of a lower olefin such as propylene, butenes or pentenes, or a mixture thereof. Particularly preferred are butenes.

As such butenes, it is preferred to employ a butene fraction having a high n-butene content, which is obtained by separating butadiene and isobutylene from a $C_4$ fraction (BB fraction) obtained by thermal cracking of a hydrocarbon oil such as naphtha. Further, a BB fraction obtained by catalytic cracking (such as FCC) of a hydrocarbon oil such as heavy oil, is a mixture composed mainly of butene and butane, and it is also preferred to employ a butene fraction having a high n-butene content which is obtained by separating isobutylene by distillation from such a BB fraction. Such butenes usually contain a substantial amount of 2-butene which is an internal olefin, in addition to 1-butene. However, the dimerization method of the present invention provides a sufficiently high activity even against an internal olefin substrate such as 2-butene.

The catalyst for the dimerization reaction to be used in the present invention is a catalyst system comprising (i) a nickel compound, (ii) an organic aluminum compound, and (iii) a phosphite compound of the formula (I):

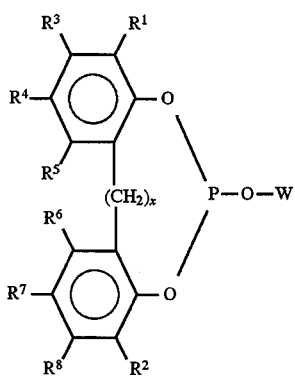

wherein each of $R^1$ and $R^2$ which may be the same or different, is a hydrocarbon group, each of $R^3$ to $R^8$ which may be the same or different, is a substituent containing no oxygen atom, or a hydrogen atom, W is a substituted or unsubstituted aromatic hydrocarbon group, and x is 0 or 1.

The nickel compound to be used in this catalyst system is not particularly limited. For example, readily available nickel compounds may be mentioned which include a nickel carboxylate such as nickel formate, nickel acetate, nickel octanoate, nickel dodecanoate, nickel naphthenate, nickel oleate or nickel benzoate, a nickel complex compound such as nickel bis(acetylacetonate) or nickel bis(cyclooctadiene), and an inorganic acid salt of nickel such as nickel chloride, nickel bromide, nickel iodide, nickel nitrate or nickel sulfate. Among these nickel compounds, particularly preferred are $C_{1-18}$ nickel carboxylates and nickel bis(acetylacetonate) complex compounds.

The organic aluminum compound is also not particularly limited. For example, it may be a trialkylaluminum compound of the formula $AlR_3$ (wherein R is a $C_{1-5}$ alkyl group), specifically trimethylaluminum, triethylaluminum, tri-n-propylaluminum, tri-n-butylaluminum, triisopropylaluminum, triisobutylaluminum, or tri-t-butylaluminum, or a monohalogenodialkylaluminum, dihalogenomonoalkylaluminum or sesquihalogenoalkylaluminum compound of the formula $AlR_2X$, $AlRX_2$ or $Al_2R_3X_3$ (wherein R is a $C_{1-5}$ alkyl group, and X is a halogen atom), specifically diethylaluminum monochloride, ethylaluminum dichloride, ethylaluminum sesquichloride, propylaluminum dichloride or isobutylaluminum dichloride, or an organic aluminoxane compound obtained by partial hydrolysis of the above-mentioned trialkylaluminum or halogenoalkylaluminum. Among these organic aluminum compounds, haloge- nated alkylaluminum compounds are preferred. Particularly preferred among them is a dihalogenomonoalkylaluminum compound such as ethylaluminum dichloride.

According to the method of the present invention, by incorporating the above-mentioned specific phosphite compound of the formula (I) to the basic catalyst system comprising the nickel compound and the organic aluminum compound, it is possible to obtain a dimerized olefin mixture highly selectively with high catalytic activity as compared with the conventional catalyst systems. If the above-mentioned phosphite compound is absent as a catalyst constituting component or if other phosphite compound which has no ring structure in the phosphite structure and which has no substituent which provides a steric hindrance in the vicinity of the oxygen atom of the P—O bond portion, such as triphenyl phosphite or triethyl phosphite, is employed, the dimerization activity is low, and the catalytic performance is not necessarily satisfactory.

The phosphite compound to be used in the present invention is represented by the above formula (I).

In the above formula, the group represented by each of $R^3$ to $R^8$ may be a group containing no oxygen atom, or a hydrogen atom. The group containing no oxygen atom may, for example, be an alkyl group, an aryl group, a cycloalkyl group or a halogen atom. Specifically, it may, for example, be a $C_{1-20}$ alkyl group such as a methyl group, an ethyl group, a propyl group, a butyl group, a hexyl group, a nonyl group or an octadecyl group, a $C_{6-12}$ aryl group such as a phenyl group or a naphthyl group, a $C_{4-12}$ cycloalkyl group such as a cyclohexyl group, or a halogen atom such as a chlorine atom or a bromine atom. Among them, an alkyl group, particularly a $C_{1-20}$ alkyl group, is preferred. The groups represented by $R^3$ to $R^8$ may be the same or different from one another. When easiness in the synthesis of the phosphite compound is taken into consideration, it is preferred that each of $R^3$, $R^5$, $R^6$ and $R^8$ is a hydrogen atom, and particularly preferred is a combination in which each of $R^4$ and $R^7$ is a $C^{1-20}$ alkyl group.

For the phosphite compound to be used in the present invention, it is very important for improving the activity for the dimerization reaction that each of $R^1$ and $R^2$ in the above formula (I) is a hydrocarbon group. The hydrocarbon group for each of $R^1$ and $R^2$ may, for example, be a $C_{1-20}$ alkyl group, a $C_{6-12}$ aryl group or a $C_{4-12}$ cycloalkyl group. The substituents for $R^1$ and $R^2$ are bulky as a whole, although such may vary depending upon the steric hindrance of the group represented by W in the formula (I), as described hereinafter. Accordingly, the hydrocarbon group for each of $R^1$ and $R^2$ is usually a branched alkyl group, preferably a $C_{3-10}$ branched alkyl group, specifically an i-propyl group, a s-butyl group, a t-butyl group, a s-amyl group, a t-amyl group, a t-hexyl group, a cyclohexyl group, or a 1-methylcyclohexyl group. $R^1$ and $R^2$ may be the same or different from each other.

In the above formula (I), W is an aromatic hydrocarbon group. Such an aromatic hydrocarbon group may, for example, be a phenyl group, a 2-naphthyl group or an anthryl group. This aromatic hydrocarbon group may not have a substituent, but preferably has a substituent. Among them, particularly preferred is a substituted phenyl group.

The substituent for the aromatic hydrocarbon group may, for example, be an alkyl group, an aryl group, a cycloalkyl group or a halogen atom, specifically a $C_{1-20}$ alkyl group such as a methyl group, an ethyl group, a propyl group, a i-propyl group, a butyl group, a s-butyl group, a t-butyl group, an amyl group, a hexyl group, an octyl group, a nonyl group or a octadecyl group, a $C_{6-12}$ aryl group such as a phenyl group or a naphthyl group, a $C_{4-12}$ cycloalkyl group such as a cyclohexyl group, or a halogen atom such as a chlorine atom or a bromine atom. Among them, an alkyl group, particularly a $C_{1-20}$ alkyl group, is preferred.

The aromatic hydrocarbon group for W preferably has a substituent on a carbon atom adjacent to the carbon atom bonded to the oxygen atom constituting the P—O bond (e.g. at the o-position in a phenyl group, hereinafter generally referred to as the o-position including cases other than a phenyl group). As such a substituent, a substituent such as a methyl group, an ethyl group, an i-propyl group, a s-butyl group, a t-butyl group, a s-amyl group, a t-amyl group, a t-hexyl group, a cyclohexyl group or a phenyl group may, for example, be mentioned. Among them, a substituent having from 3 to 10 carbon atoms (such as a $C_{3-10}$ hydrocarbon group) is preferred with a view to attaining a high activity for the dimerization reaction.

Further, in a case where $R^1$ and $R^2$ are bulky substituents and the substituent at the o-position of W is a methyl group, an ethyl group, an i-propyl group or a s-butyl group, it is possible to obtain an effect such that the average branching degree decreases, for example, when a dimerization reaction of butenes is carried out, the content of dimethylhexene in the formed octenes decreases. Accordingly, this provides an excellent performance when the formed olefin is hydroformylated and further hydrogenated to obtain an alcohol, and the alcohol is reacted and esterified with a carboxylic acid such as phthalic acid to use the product as a plasticizer for synthetic resins.

In the above formula (I), x in the linking group of the formula $-\!\!-\!\!(CH_2)\!\!-\!\!_x$ is 0 or 1, and in either case, the activity and the selectivity are good. Even then, depending upon the value of x, the distribution or the selectivity for the dimerization product varies substantially. For example, in a case where a dimerization reaction of butenes is carried out by the catalyst system of the present invention, when x=0 i.e. when the linking group is a single bond, relatively less branched octenes will form highly selectively under a high activity. Whereas, when x=1 i.e. when the linking group is a methylene group, the branching degree of formed octenes tends to be high, and the selectivity for the dimerization product will further be improved, and an extremely high selectivity will be obtained even under a high conversion condition. This means that the desired product can be produced highly economically, and thus provides a substantial value for industrial application.

The details of the function of the phosphite compound of the formula (I) to the structure or the reactivity of the dimerization catalyst are not known. However, it is considered that each of the crosslinked two substituted phenyl groups and the aromatic hydrocarbon group represented by W in the formula (I), has a substituent at the o-position, whereby an undesirable reaction with an organoaluminum compound as a Lewis acid will be prevented, and consequently, the stable and active catalyst structure is believed to be maintained.

The method for preparing the phosphite compound of the formula (I) is not particularly limited. However, it can be readily prepared, for example, by reacting a compound of the formula (II):

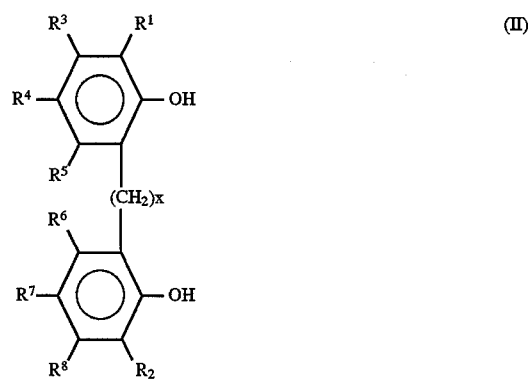

(wherein $R^1$ to $R^8$ and x are as defined in the formula (I)) and phosphorus trichloride in a solvent such as toluene in the presence of an amine compound, to form an intermediate of the formula (III):

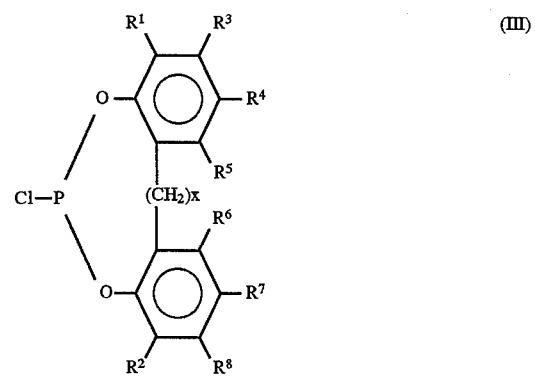

(wherein $R^1$ to $R^8$ and x are as defined in the formula (I)), and reacting this intermediate of the formula (III) with a compound of the formula (IV):

(wherein W is as defined in the above formula (I)) to convert it to the corresponding phosphite compound.

The above-mentioned compound of the formula (IV) may, for example, be phenol, 2-methylphenol, 2,4-dimethylphenol, 2,4,6-trimethylphenol, 2-t-butylphenol, 2,4-di-t-butylphenol, 2-s-butylphenol, 2,4-di-s-butylphenol, 2-isopropylphenol, 2-t-amylphenol, 2-s-amylphenol, 2-t-hexylphenol, 2,4-di-t-amylphenol, 6-t-butyl-2,4-xylenol, 2,4-dichlorophenol, 2,4,6-trichlorophenol, 3-t-butyl-4-hydroxybiphenyl, 2-t-butyl-p-cresol, 2-hydroxybiphenyl, 2-cyclohexylphenol, 2-naphthol, 3-isopropyl-2-naphthol, 3,6-diisopropyl-2-naphthol, 3-t-butyl-2-naphthol, 3,6-di-t-butyl-2-naphthol, 3,6-di-s-butyl-2-naphthol, 3-t-amyl-2-naphthol, 3,6-di-t-amyl-2-naphthol, 3-t-hexyl-2-naphthol, 3-phenyl-2-naphthol, 3,6-diphenyl-2-naphthol or 3-cyclohexyl-2-naphthol.

Further, the above-mentioned compound of the formula (II) may, for example, be 3,3',5,5'-tetramethyl-2,2'-biphenyldiol, 5,5'-dimethyl-3,3'-diethyl-2,2'-biphenyldiol, 5,5'-dimethyl-3,3'-di-t-butyl-2,2'-biphenyldiol, 5,5'-diethyl-3,3'-di-t-butyl-2,2'-biphenyldiol, 5,5'-dichloro-3,3'-di-t-butyl-2,2'-biphenyldiol, 3,3',5,5'-tetra-t-butyl-2,2'-biphenyldiol, 5,5'-di-t-butyl-3,3'-diphenyl-2,2'-biphenyldiol, 5,5'-di-t-butyl-3,3'-diisopropyl-2,2'-biphenyldiol, 5,5'-dimethyl-3,3'-di-t-amyl-2,2'-biphenyldiol, 5,5'-di-t-hexyl-3,3'-di-t-butyl-2,2'-biphenyldiol, 2,2'-methylenebis(4-methyl-6-t-butylphenol), 2,2'-methylenebis(4-ethyl-6-t-butylphenol), 2,2'-methylenebis(4,6-diisopropylphenol), 2,2'-methylenebis(4,6-di-t-butylphenol) or 2,2'-methylenebis(4-chloro-6-t-butylphenol).
Typical examples of the phosphite compound of the formula (I) to be used in the present invention will be shown below.
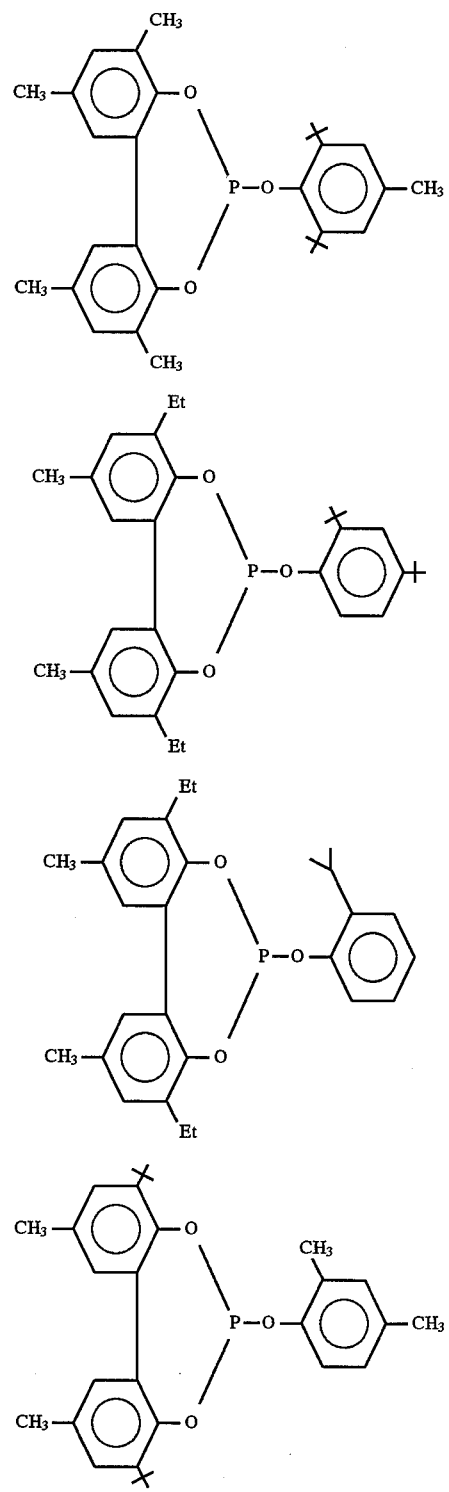
-continued
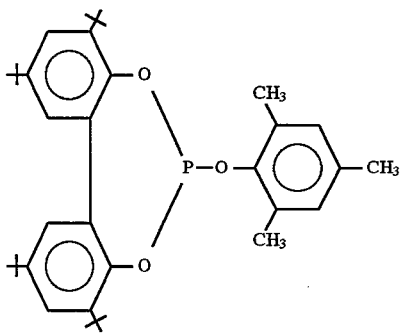
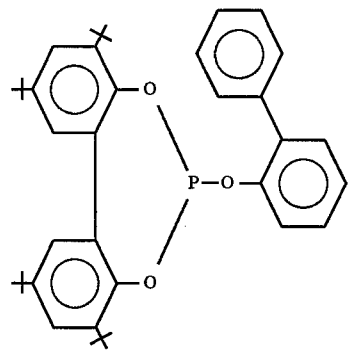
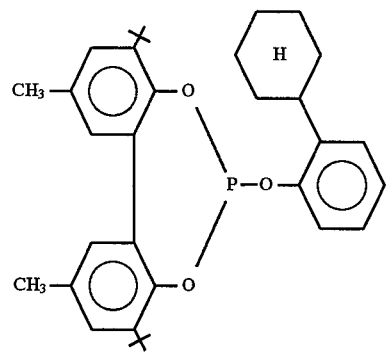
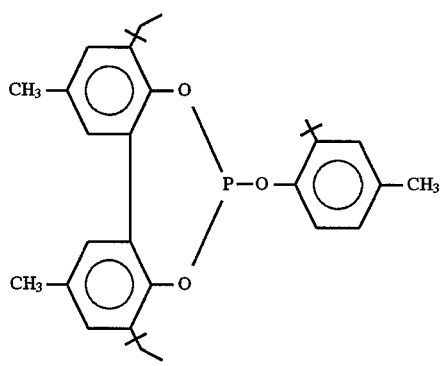

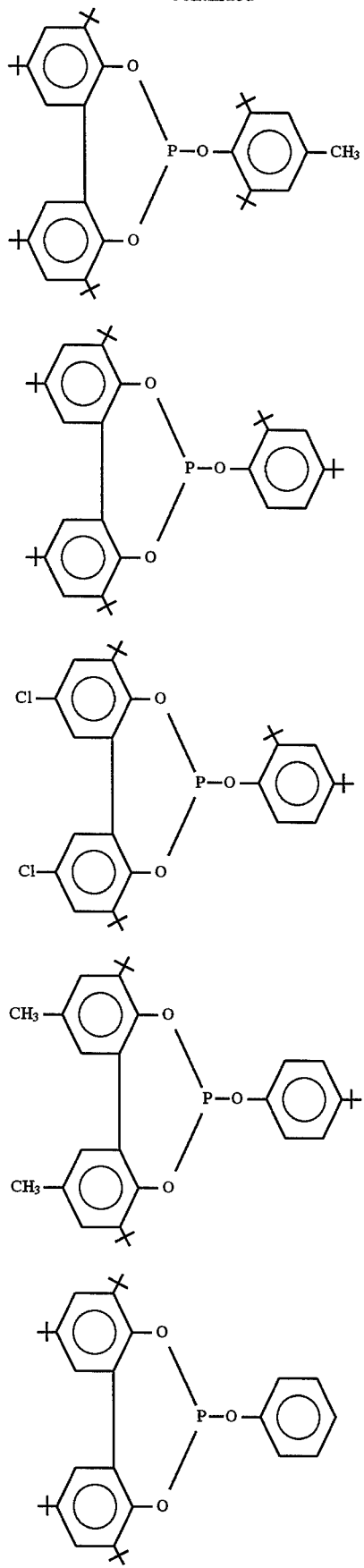
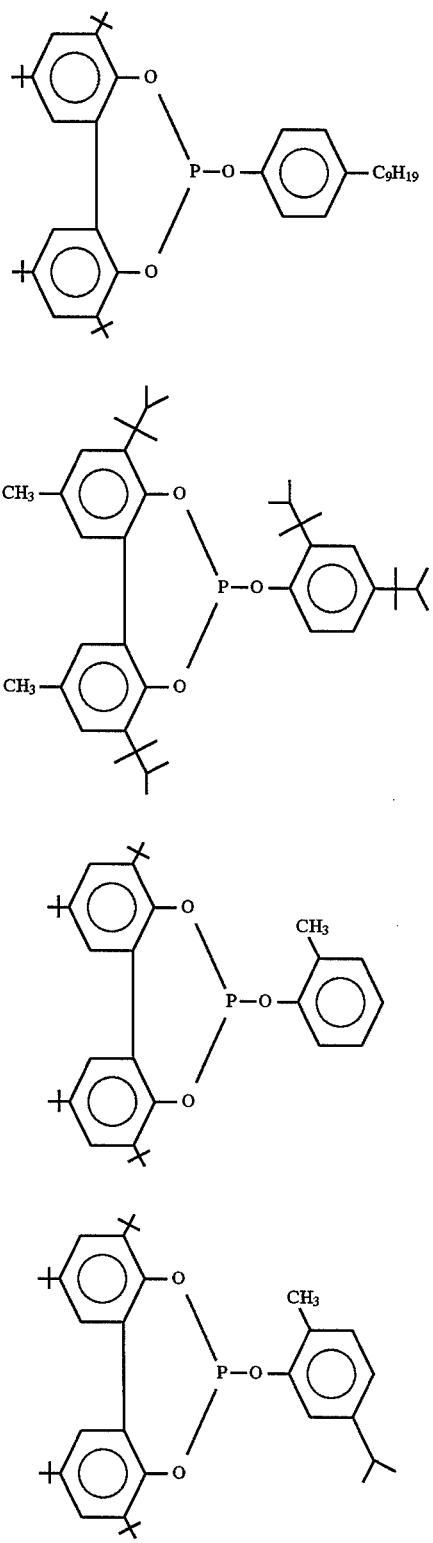

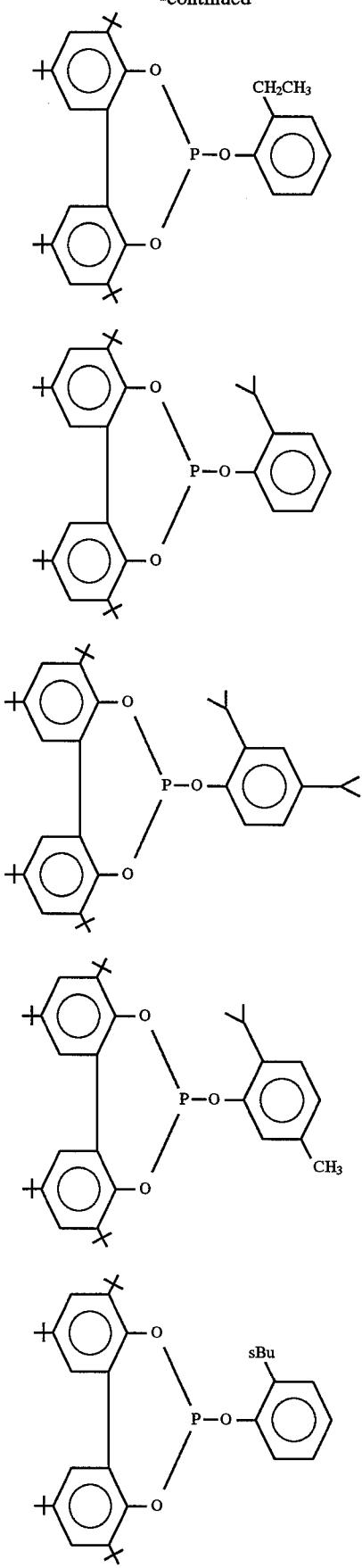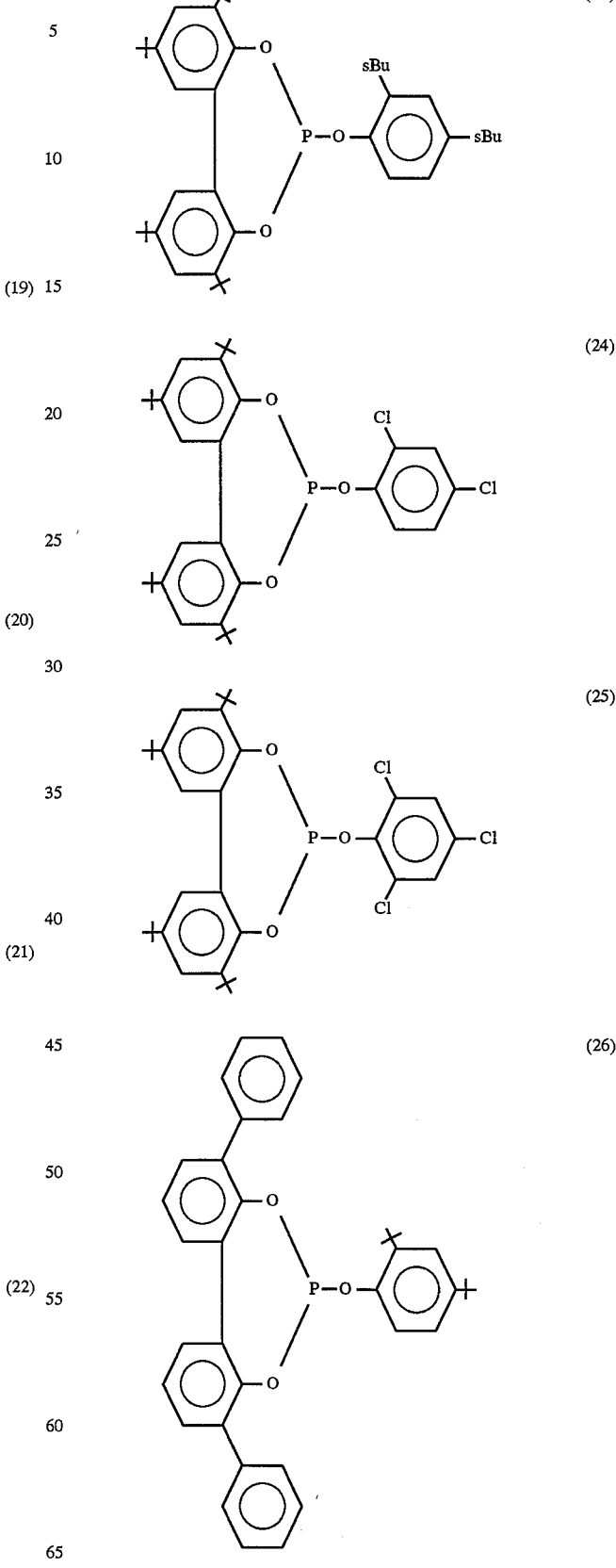

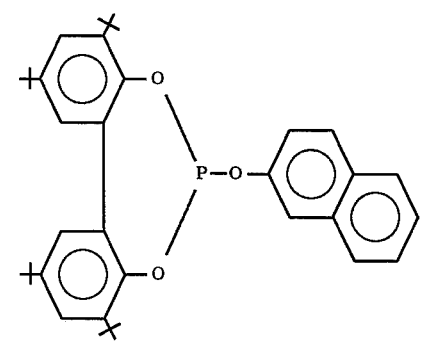
(27)
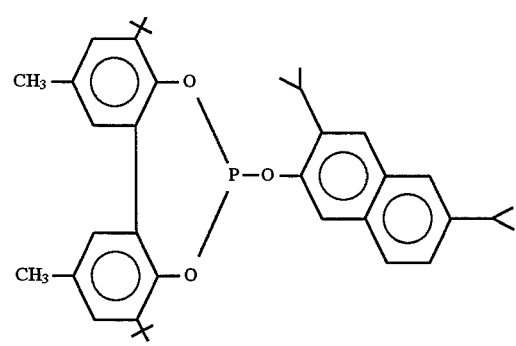
(28)
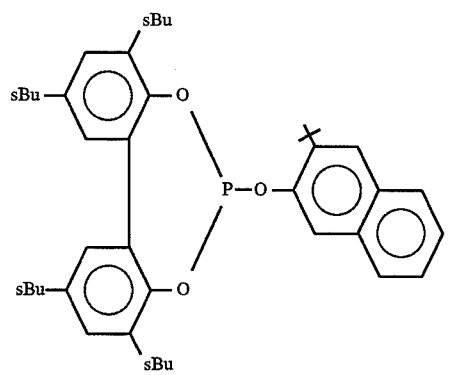
(29)
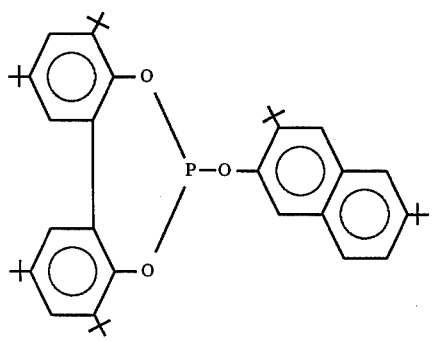
(30)
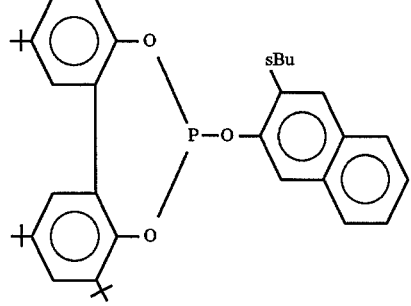
(31)
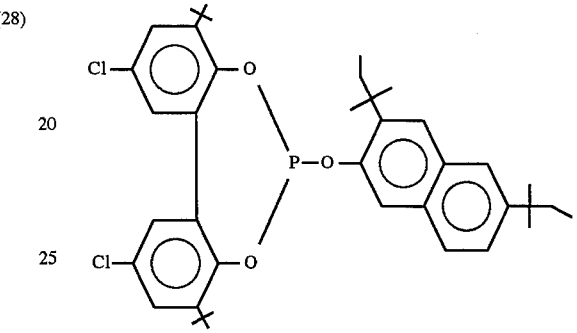
(32)
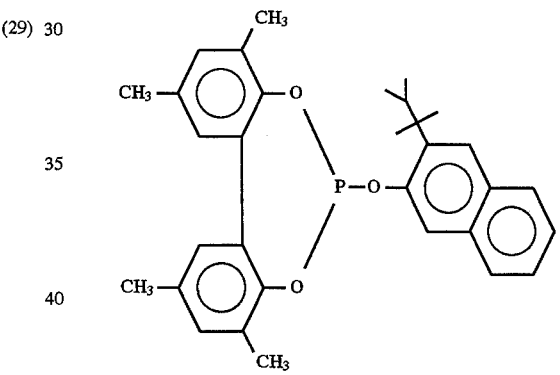
(33)
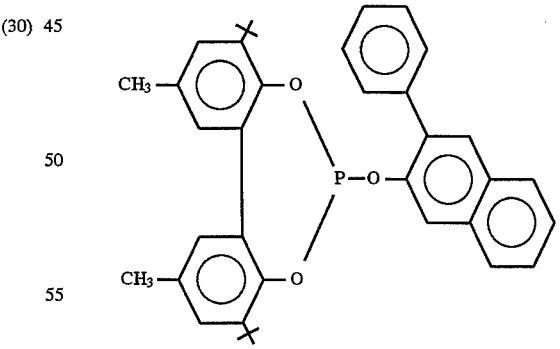
(34)

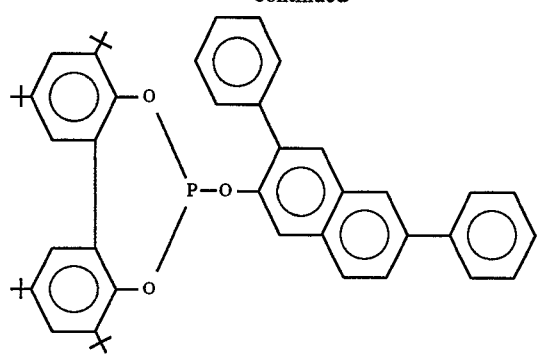
(35)
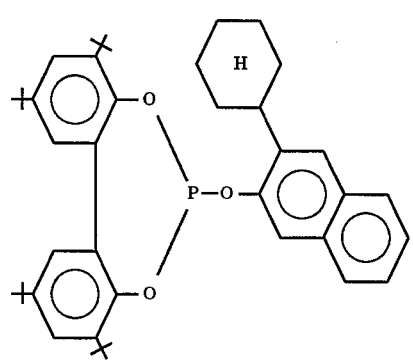
(36)
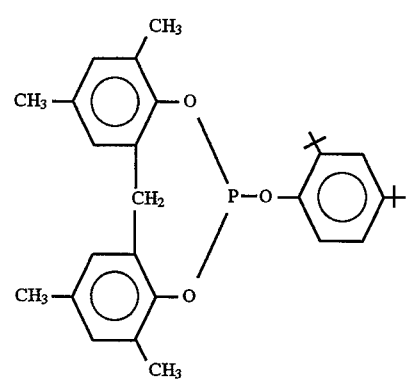
(37)
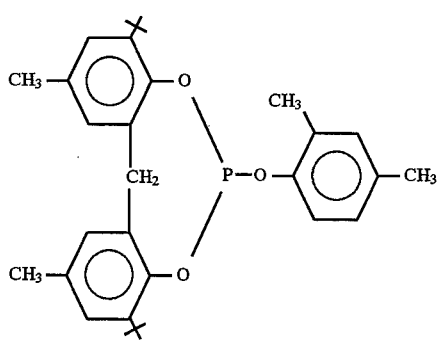
(38)
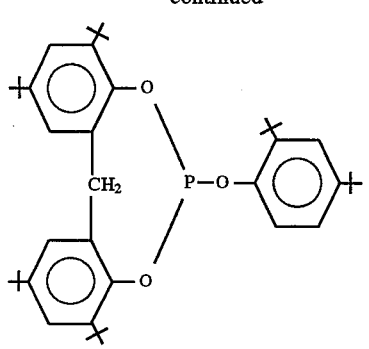
(39)
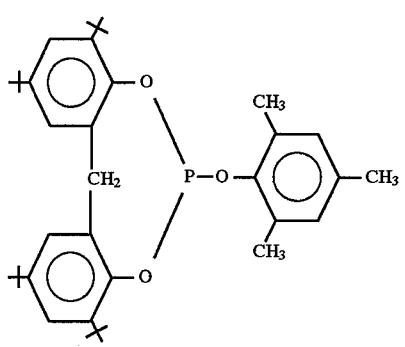
(40)
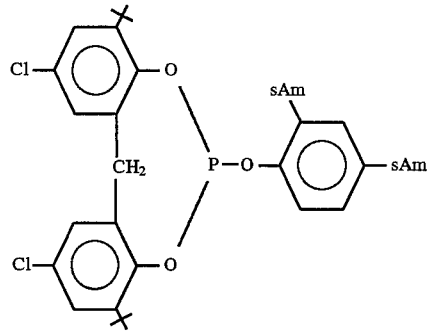
(41)
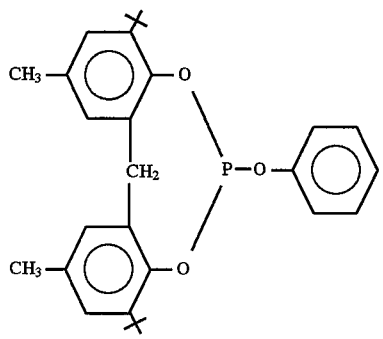
(42)

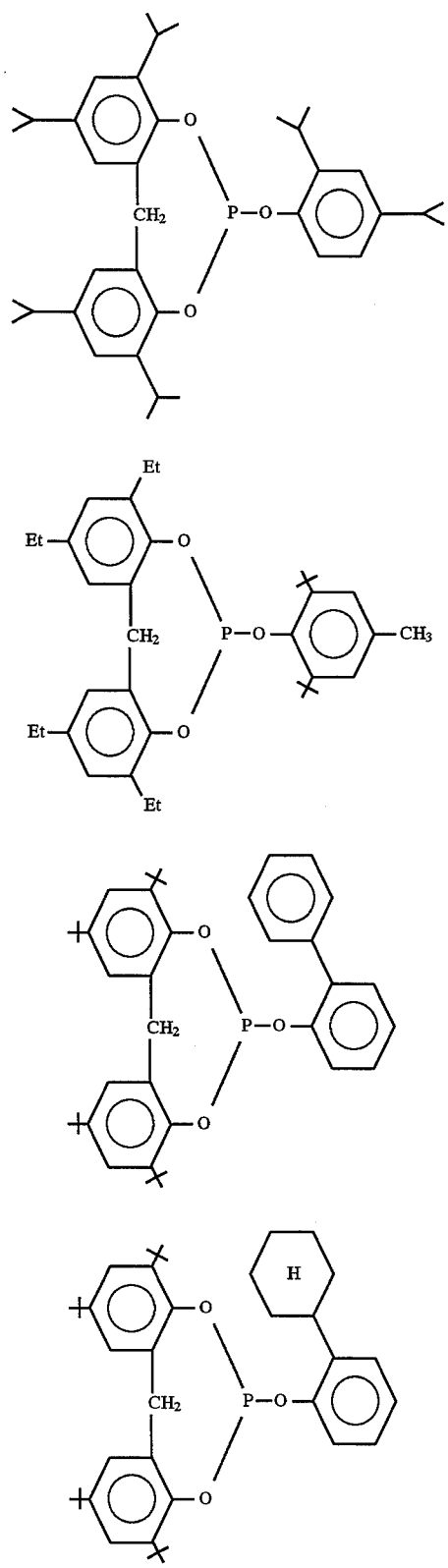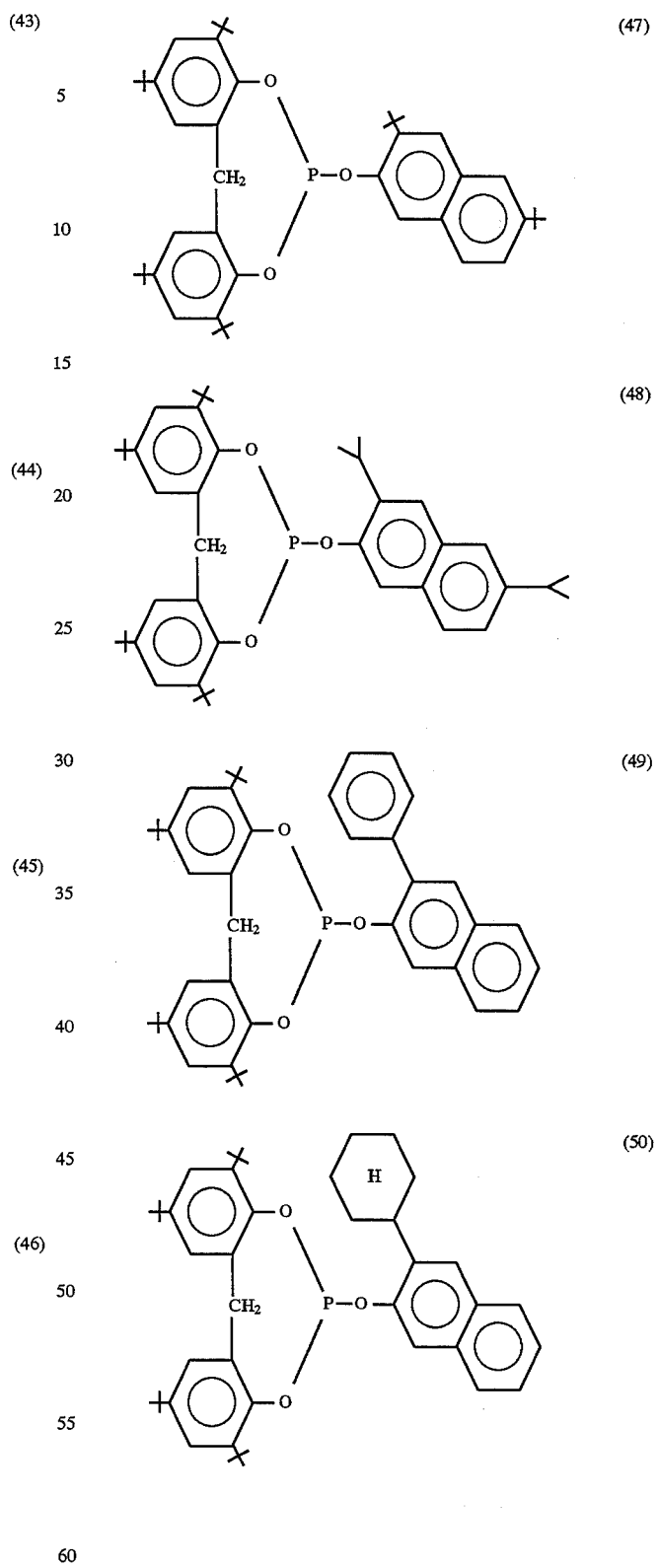

-continued

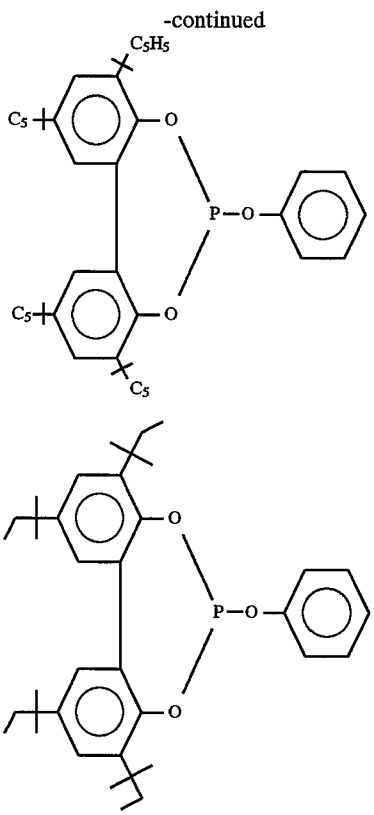

(51)

(52)

The symbols used in the above structural formulas represent the following substituents.

Tertiary butyl group,

Isopropyl group,

Tertiary amyl group,

tertiary hexyl group,
sBu: Secondary butyl group, sAm: Secondary amyl group,
$C_5+$: 1,1-Dimethylhexyl group.

In the method of the present invention, the dimerization reaction of an olefin is carried out in the presence of a catalyst system comprising the above-mentioned nickel compound, the organic aluminum compound and the phosphite compound of the formula (I). At that time, if hydrogen is present in the reaction system, the catalytic activity can further be improved. Such a mechanism is not clearly understood. However, various mechanisms may be assumed such as removal of impurities (such as a reaction inhibiting substance such as a conjugated diene) in the reaction system, promotion of the formation of catalytic active species and contribution to the stability of the catalyst, and at any rate, the activity of the dimerization reaction will evidently increase by the presence of hydrogen. The amount of hydrogen is not particularly limited, and it is employed in an amount sufficient to bring about a desirable result to the catalytic activity and is usually in an amount of from 0.01 to 30 $kg/cm^2$, preferably from 0.1 to 20 $kg/cm^2$ as hydrogen partial pressure.

In the dimerization reaction of an olefin to be carried out by the present invention, the respective catalyst components i.e. the nickel compound, the organic aluminum compound and the phosphite compound of the formula (I), may be mixed in any order. However, it is preferred to preliminarily mix the nickel compound and the phosphite compound of the formula (I) or to use them in the form of their complex. Further, it is preferred to simultaneously contact these Ni—P compound and the organic aluminum compound in the presence of an olefin such as butenes with a view to obtaining dimerization products such as octenes under a high activity. This is believed attributable to the fact that the organic aluminum compound usually acts as a strong reducing agent, and when an electron donative ligand such as an olefin is not present, the nickel compound will be reduced, whereby the activity will decrease.

In the method of the present invention, it is not essential to use a solvent for the reaction. However, a solvent inert to the reaction, for example, an aromatic hydrocarbon such as benzene, toluene, xylene or dodecylbenzene, an aliphatic hydrocarbon such as hexane, heptane or cyclohexane, or a halogenated aromatic hydrocarbon such as chlorobenzene, may be employed.

The concentration of the nickel component in the liquid phase for the dimerization reaction is usually from $10^{-2}$ to $10^2$ mmol/l. The molar ratios of the respective catalyst components are influential over the dimerization activity and the product distribution. However, the molar ratio of the organic aluminum compound to the nickel compound in the catalyst in the present invention is usually from 2 to 100, preferably from 5 to 50. Further, the molar ratio of the phosphite compound of the formula (I) to the nickel compound is usually from 0.1 to 20, preferably from 1 to 5.

If the molar ratio of the organic aluminum compound to the nickel compound in the catalyst is too low, the catalyst activity sharply decreases due to the reaction with oxygen or moisture present in a very small amount in the dimerization reaction system. On the other hand, if the reaction is conducted under such a condition that such a molar ratio is unnecessarily high, no substantial additional improvement will be observed in the dimerization activity, and such is not economically advantageous. If the molar ratio of the above phosphite compound to the nickel compound is too low, the dimerization activity will decrease, and the branching degree of the formed olefin tends to increase. On the other hand, if the molar ratio is too high, the dimerization activity tends to decrease, although such may also depend on the amount of the organic aluminum compound present, and such is not economically advantageous.

With respect to the reaction conditions for dimerization carried out by the present invention, the reaction temperature is usually from −10° to 100° C., preferably from 0° to 80° C., more preferably from 10° to 80° C. The temperature is properly set depending upon the productivity of the process, the stability of the nickel compound and the organic aluminum compound used, etc.

The reaction pressure is effective so that the catalyst components are sufficiently present in the liquid phase of the olefin such as butenes, and is preferably at a level of from 1 to 50 kg/cm². Further, the dimerization method of the present invention can be carried out even if the starting material for the reaction contains a paraffin hydrocarbon such as methane, ethane, propane or butane or an inert gas such as nitrogen, argon or carbon dioxide. The system for the dimerization reaction may be a continuous system or a batch system.

After completion of the reaction, the catalyst is inactivated by a known method, for example, with aqueous ammonia, an aqueous sodium hydroxide solution or an aqueous sulfuric acid solution, and then the catalyst is removed. Then, by distillation, any non-converted olefin and the reaction solvent are separated to obtain the product.

As mentioned above, the dimerization product of an olefin produced by the dimerization method of the present invention can be hydroformylated by reacting it with carbon monoxide and hydrogen in the presence of a Group VIII metal catalyst such as a Rh catalyst, and the obtained aldehyde can be further hydrogenated to obtain an alcohol.

The above hydroformylation reaction can be carried out by a conventional method. The reaction conditions for the hydroformylation reaction are not particularly critical, and a conventional rhodium method or cobalt method may be employed.

As the rhodium source in the case of the rhodium method, an organic salt such as $Rh(OAc)_3$, an inorganic salt such as $Rh(NO_3)_3$ or $RhCl_3$, or a complex such as $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$ or $[RhCl(COD)]_2$ (wherein Ac is an actyl group, acac is an acetyl acetonate group, and COD is a cyclooctadiene, respectively) may be employed.

As the cobalt source in the case of the cobalt method, an organic salt such as cobalt laurate, an inorganic salt such as $Co(NO_3)_2$, or a complex such as $Co_2(CO)_8$ or $CoH(CO)_4$ may be employed.

The pressure for the reaction is usually from atmospheric pressure to 300 kg/cm²G, and the reaction temperature is usually from 50° C. to 150° C. The molar ratio of $H_2/CO$ is usually from 1 to 10. The catalyst concentration is usually from 0.1 to 1000 ppm (as calculated as the metal atom). As the ligand, an organic phosphorus compound such as triphenylphosphine or triphenylphosphite, or its oxide may be used usually in a molar ratio within a range of from 1 to 1000 relative to the above catalyst.

No solvent may be used for the reaction. However, a solvent inert to the reaction, for example, an aromatic hydrocarbon such as benzene, toluene, xylene or dodecylbenzene, an aliphatic hydrocarbon such as hexane, heptane or cyclohexane, an ether such as dibutyl ether, ethylene glycol dimethyl ether, triethylene glycol dimethyl ether or tetrahydrofuran, or an ester such as diethyl phthalate or dioctyl phthalate, may be used as the case requires. Otherwise, an aldehyde or an alcohol formed by the hydroformylation reaction may be used as the solvent. Further, a high boiling point by-product such as a polycondensation product of aldehyde may also be employed. The system for the reaction may be a continuous system or a batch system.

Then, by the hydrogenation reaction of the obtained aldehyde, an alcohol is produced. This reaction can be conducted by a conventional method. Namely, the reaction can be conducted by using a conventional hydrogenation catalyst such as Ni, Cr or Cu usually under a reaction pressure of from atmospheric pressure to 150 kg/cm²G at a reaction temperature of from 40° C. to 300° C. Then, by a conventional purification by distillation, the alcohol can be obtained.

The alcohol thus obtained, particularly a $C_9$ alcohol (so-called isononyl alcohol: INA) produced by using butenes as the starting material, may be esterified with an acid such as phthalic anhydride or adipic acid by a conventional method, followed by purification to obtain a plasticizer (e.g. a phthalate plasticizer). The obtained plasticizer has excellent properties.

Now, the present invention will be described in further detail with reference to Examples. However, it should be understood that the present invention is by no means restricted to such specific Examples.

EXAMPLE 1

Into a stainless steel micro autoclave having an internal capacity of 70 ml, which was deaerated and flushed with nitrogen, a m-xylene solution containing 8.28 mg of nickel octanoate and 3 mols per mol of the nickel atom (P/Ni=3) of the above-mentioned phosphite compound (10) and a pentane solution containing 38.1 mg (Al/Ni=12.5) of dichloroethylaluminum, were charged under a nitrogen atmosphere. Then, 20 ml of trans-2-butene was charged, and the micro autoclave was closed, whereupon a reaction was carried out at 40° C. for 5 hours with stirring. After completion of the reaction, the micro autoclave was cooled to room temperature, and any unreacted gas was purged. Then, 2 ml of methanol was added thereto to terminate the reaction.

The reaction solution was subjected to gas chromatography (column: CBP1 capillary 0.25φ×50 m and 10% SE-30/Chromosorb 2m, manufactured by Shimadzu Corporation) to analyze the concentrations of the products. The results are shown in Table 1.

Comparative Example 1

A dimerization reaction of trans-2-butene was carried out in the same manner as in Example 1 except that no phosphite compound was added.

The results of the reaction are shown in Table 1.

Comparative Examples 2 and 3

Dimerization reactions of trans-2-butene were carried out in the same manner as in Example 1, except that instead of the phosphite compound (10), triphenylphosphite and triethylphosphite were, respectively, employed in a proportion of 3 mols per mol of the nickel atom (P/Ni=3).

The results of the reactions are shown in Table 1.

EXAMPLES 2 TO 10

Dimerization reactions of trans-2-butene were carried out in the same manner as in Example 1, except that instead of the phosphite compound (10), various phosphite compounds as identified in Table 1 were used in a proportion of 3 mols of the phosphorus atom per mol of the nickel atom (P/Ni=3).

The results of the reactions are shown in Table 1.

Comparative Example 4

A dimerization reaction of trans-2-butene was carried out in the same manner as in Example 7, except that instead of the phosphite compound (9), a phosphite compound as identified in Table 1 was used in a proportion of 3 mols per mol of the nickel atom (P/Ni=3).

The results of the reaction are shown in Table 1.

EXAMPLES 11 TO 16

Dimerization reactions of trans-2-butene were carried out in the same manner as in Example 1, except that instead of the phosphite compound (10), various phosphite compounds as identified in Table 1 were used in a proportion of 1 mol of the phosphorus atom per mol of the nickel atom (P/Ni=1), and the dimerization reactions were conducted at 60° C. for 3 hours.

The results of the reactions are shown in Table 1.

EXAMPLE 17

A dimerization reaction of trans-2-butene was carried out in the same manner as in Example 12, except that instead of dichloroethylaluminum, ethylaluminum sesquichloride was used in a proportion of 25 mols of the aluminum atom per mol of the nickel atom (Al/Ni=25).

The results of the reaction are shown in Table 1.

EXAMPLE 18

A dimerization reaction of trans-2-butene was carried out in the same manner as in Example 1, except that after charging trans-2-butene, hydrogen gas was introduced until the total pressure became 5 kg/cm$^2$G.

The results of the reaction are shown in Table 1.

Comparative Example 5

A dimerization reaction of trans-2-butene was carried out in the same manner as in Example 18, except that no phosphite compound was added.

The results of the reaction are shown in Table 1.

Comparative Examples 6 and 7

Dimerization reactions of trans-2-butene were carried out in the same manner as in Example 18, except that instead of the phosphite compound (10), triphenylphosphite and triethylphosphite were, respectively, used in a proportion of 3 mols per mol of the nickel atom (P/Ni=3).

The results of the reactions are shown in Table 1.

EXAMPLES 19 to 21

Dimerization reactions of trans-2-butene were carried out in the same manner as in Example 18, except that instead of the phosphite compound (10), various phosphite compounds as identified in Table 1 were used in a proportion of 3 mols per mol of the nickel atom (P/Ni=3).

The results of the reactions are shown in Table 1.

EXAMPLE 22

Into a stainless steel autoclave having an internal capacity of 300 ml, which was deaerated and flushed with nitrogen, 3.76 ml of a heptane solution containing 0.2 mol/l of dichloroethylaluminum, was charged under a nitrogen atmosphere. Then, 29.2 g (520 mmol) of trans-2-butene was injected, and the autoclave was heated to 60° C. with stirring. After the temperature reached 60° C., a heptane solution containing 20.7 mg of nickel octanoate and 1 mol per mol of the nickel atom (P/Ni=1) of the above-mentioned phosphite compound (19), was injected with purified hydrogen to initiate the reaction, and the reaction was carried out for one hour.

The results of the reaction are shown in Table 1.

EXAMPLE 23

Into a stainless steel induction type autoclave having an internal capacity of 5 l, which was deaerated and flushed with nitrogen, 25.6 ml of a heptane solution containing 0.1 mol/l of dichloroethylaluminum and 100 ml of cyclohexane were charged under a dry nitrogen atmosphere. Then, 1.78 kg (31.72 mol) of 1-butene which was dehydrated by a molecular sieve, was injected.

With stirring at room temperature, 20.5 ml of a heptane solution containing 0.1 mol/l of nickel octanoate and a heptane solution containing the above-mentioned phosphite compound (19) in an amount of 1 mol per mol of the nickel atom (P/Ni=1), were injected into the autoclave with dry nitrogen to initiate the reaction. Immediately, the temperature and pressure rise in the autoclave was observed, but the temperature was maintained at a level of 60° C. by using an external cooler and an external heater, and the reaction was conducted for 3 hours.

After expiration of 3 hours, 50 ml of methanol was injected into the autoclave to terminate the reaction, and the autoclave was cooled to room temperature. Then, any unreacted gas was purged, and the concentrations of the products in the reaction solution were analyzed by gas chromatography. The results are shown in Table 2.

EXAMPLE 24

A dimerization reaction of 1-butene was carried out in the same manner as in Example 23, except that the catalyst components i.e. dichloroethylaluminum, nickel octanoate and the phosphite compound, were preliminarily mixed and then 1-butene was injected to initiate the reaction. The results are shown in Table 2.

As is evident from Table 2, catalytic activities superior to the conventional technique and high selectivity can be obtained irrespective of the order of the contact of the catalyst, and even better effects can be obtained when contact of the catalyst is conducted in the presence of an olefin.

TABLE 1

| Example No. | Phosphite compound No. | Phosphite compound Chemical formula | Yield of oligomers *1 (%) C$_8$ Olefin | Yield of oligomers *1 (%) C$_{12}$ Olefin< | C$_8$ Olefin structure distribution *2 (%) n-form | C$_8$ Olefin structure distribution *2 (%) 3-Me-form | C$_8$ Olefin structure distribution *2 (%) 3,4-Me$_2$-form |
|---|---|---|---|---|---|---|---|
| Example 1 | (10) | [structure] | 69.1 | 11.1 | 8.5 | 78.5 | 13.0 |
| Comparative Example 1 | — | — | 29.3 | 1.3 | 5.1 | 63.8 | 31.0 |
| Comparative Example 2 | — | P(O-Ph)$_3$ | 14.1 | trace | 3.6 | 70.7 | 25.8 |
| Comparative Example 3 | — | P(OC$_2$H$_5$)$_3$ | 5.4 | 2.0 | 7.9 | 64.4 | 27.6 |
| Example 2 | (12) | [structure] | 63.6 | 5.2 | 9.4 | 82.2 | 8.4 |
| Example 3 | (13) | [structure] | 63.0 | 4.8 | 9.0 | 82.4 | 8.6 |
| Example 4 | (30) | [structure] | 62.8 | 3.6 | 6.3 | 78.5 | 15.2 |

TABLE 1-continued

| Example No. | Phosphite compound No. | Chemical formula | Yield of oligomers *1 (%) $C_8$ Olefin | $C_{12}$ Olefin< | $C_8$ Olefin structure distribution *2 (%) n-form | 3-Me-form | 3,4-$Me_2$-form |
|---|---|---|---|---|---|---|---|
| Example 5 | (6) | [structure] | 60.7 | 4.9 | 8.0 | 81.5 | 10.5 |
| Example 6 | (11) | [structure] | 65.3 | 10.3 | 8.2 | 78.4 | 13.4 |
| Example 7 | (9) | [structure] | 50.5 | 1.7 | 7.5 | 79.0 | 13.5 |
| Example 8 | (39) | [structure] | 56.6 | 2.4 | 2.0 | 45.4 | 52.6 |
| Comparative Example 4 | — | [structure] | 21.3 | 0.9 | 3.7 | 57.5 | 38.9 |

TABLE 1-continued
| Example No. | Phosphite compound No. | Chemical formula | Yield of oligomers *1 (%) C₈ Olefin | C₁₂ Olefin< | C₈ Olefin structure distribution *2 (%) n-form | 3-Me-form | 3,4-Me₂- form |
|---|---|---|---|---|---|---|---|
| Example 9 | (51) | 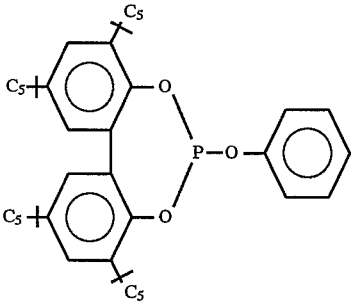 | 61.1 | 4.0 | 10.4 | 80.4 | 9.3 |
| Example 10 | (52) | 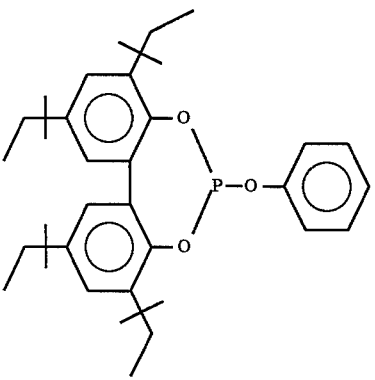 | 61.6 | 4.8 | 10.0 | 81.1 | 8.9 |
| Example 11 | (10) | 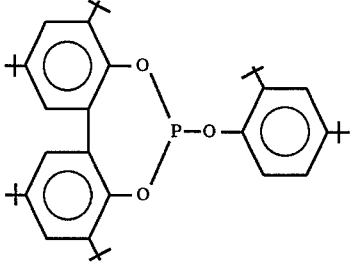 | 66.7 | 18.9 | 5.9 | 77.5 | 16.7 |
| Example 12 | (19) | 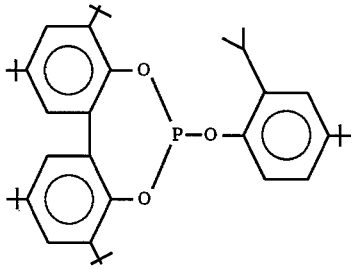 | 70.7 | 12.8 | 10.3 | 83.0 | 6.7 |
| Example 13 | (22) | 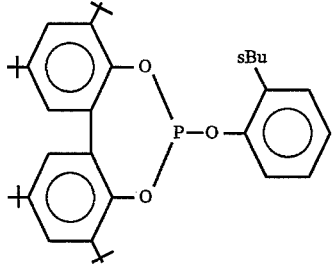 | 74.1 | 15.0 | 8.4 | 83.0 | 8.6 |

TABLE 1-continued

| | Phosphite compound | | Yield of oligomers *[1] (%) | | $C_8$ Olefin structure distribution *[2] (%) | | |
|---|---|---|---|---|---|---|---|
| Example No. | No. | Chemical formula | $C_8$ Olefin | $C_{12}$ Olefin< | n-form | 3-Me-form | 3,4-Me$_2$-form |
| Example 14 | (18) | | 68.8 | 10.7 | 11.0 | 82.8 | 6.2 |
| Example 15 | (17) | | 69.6 | 10.8 | 12.0 | 82.0 | 6.0 |
| Example 16 | (25) | | 70.8 | 11.4 | 9.5 | 81.4 | 9.1 |
| Example 17 | (19) | | 51.6 | 5.4 | 12.5 | 81.6 | 5.9 |
| Example 18 | (10) | | 72.1 | 21.9 | 4.6 | 76.4 | 19.0 |
| Comparative Example 5 | — | — | 28.2 | 0.9 | 9.3 | 60.3 | 30.4 |

TABLE 1-continued

| Example No. | No. | Chemical formula | Yield of oligomers *1 (%) | | C₈ Olefin structure distribution *2 (%) | | |
|---|---|---|---|---|---|---|---|
| | | | C₈ Olefin | C₁₂ Olefin< | n-form | 3-Me-form | 3,4-Me₂-form |
| Comparative Example 6 | — | P—(O—Ph)₃ | 36.3 | 0.5 | 3.5 | 70.8 | 25.7 |
| Comparative Example 7 | — | P(OC₂H₅)₃ | 8.4 | 2.1 | 8.0 | 64.6 | 27.6 |
| Example 19 | (13) | | 72.5 | 9.2 | 8.0 | 82.0 | 10.0 |
| Example 20 | (20) | | 71.3 | 15.8 | 5.6 | 77.4 | 17.0 |
| Example 21 | (29) | | 92.6 | 4.9 | 1.0 | 45.2 | 53.9 |
| Example 22 | (19) | | 74.9 | 13.8 | 10.4 | 82.9 | 6.7 |

*1: Weight % of the formed oligomers relative to the charged butene.
*2: Mol % of each structural isomer relative to the total octenes formed. n-form: n-octene, 3-Me-form: 3-methylheptene, 3,4-Me₂-form: 3,4-dimethylhexene.

TABLE 2

| Example No. | Phosphite compound No. | Phosphite compound Chemical formula | Yield of oligomers *1 (%) C8 Olefin | Yield of oligomers *1 (%) C12 Olefin< | C8 Olefin structure distribution *2 (%) n-form | C8 Olefin structure distribution *2 (%) 3-Me-form | C8 Olefin structure distribution *2 (%) 3,4-Me2-form |
|---|---|---|---|---|---|---|---|
| Example 23 | (19) | 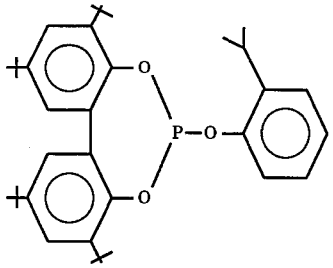 | 69.7 | 8.7 | 12.0 | 81.6 | 6.4 |
| Example 24 | (19) | 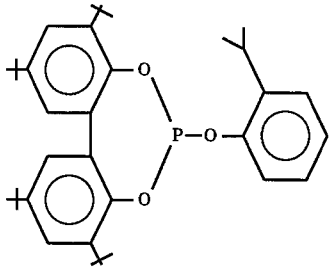 | 57.5 | 6.4 | 12.2 | 81.7 | 6.1 |

*1: Weight of the formed oligomers relative to the charged butene.
*2: Mol % of each structural isomer relative to the total octenes formed. n-form: n-octene, 3-Me-form: 3-methylheptene, 3,4-Me2-form: 3,4-dimethylhexene.

According to the present invention, an olefin can be dimerized under a high activity to obtain a dimerization product highly selectively.

What is claimed is:

1. A method for dimerizing an olefin, which comprises dimerizing an olefin in the presence of a catalyst, wherein a nickel compound, an organic aluminum compound and a phosphite compound of the formula (I):

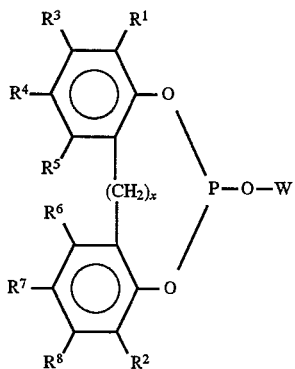

(I)

wherein each of $R^1$ and $R^2$ which may be the same or different, is a hydrocarbon group, each of $R^3$ to $R^8$ which may be the same or different, is a substituent containing no oxygen atom, or a hydrogen atom, W is a substituted or unsubstituted aromatic hydrocarbon group, and x is 0 or 1, are used as the catalyst.

2. The method according to claim 1, wherein the phosphite compound is a phosphite compound of the formula (T):

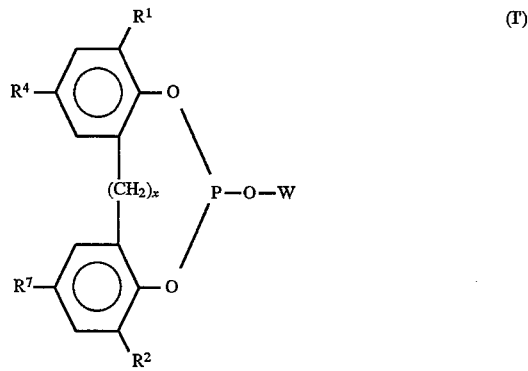

(T)

wherein each of $R^1$ and $R^2$ which may be the same or different, is a $C_{1-20}$ alkyl group, a $C_{6-12}$ aryl group or a $C_{4-12}$ cycloalkyl group, each of $R^4$ and $R^7$ which may be the same or different, is a hydrogen atom, a $C_{1-20}$ alkyl group, a $C_{1-12}$ aryl group, a $C_{4-12}$ cycloalkyl group or a halogen, W is a substituted phenyl group or a 2-naphthyl group, and x is 0 or 1.

3. The method according to claim 2, wherein each of $R^1$ and $R^2$ is a $C_{3-20}$ branched alkyl group, each of $R^4$ and $R^7$ is a $C_{1-20}$ alkyl group or a halogen, W is a phenyl group with the ortho position substituted by a $C_{1-10}$ hydrocarbon group, and x is 0.

4. The method according to claim 1, wherein the olefin is a $C_{3-5}$ olefin.

5. The method according to claim 1, wherein the nickel compound is a nickel $C_{1-18}$ carboxylate or a bis (acetylacetonate)nickel complex compound.

6. The method according to claim 1, wherein the organic aluminum compound is an alkylaluminum halide.

7. The method according to claim 1, wherein the reaction is conducted in the presence of from 0.01 to 30 kg/cm$^2$ of hydrogen.

8. The method according to claim 1, wherein the amount of the nickel compound used is such that the nickel concentration in a liquid phase would be from $10^{-2}$ to $10^2$ mmol/l, and the amount of the organic aluminum compound used is from 2 to 100 as the molar ratio to the nickel compound, and the amount of the phosphite compound used is from 0.1 to 20 as the molar ratio to the nickel compound.

9. The method according to claim 1, wherein the reaction temperature is from −10° to 100° C., and the reaction pressure is from 1 to 50 kg/cm$^2$.

10. The method according to claim 1, wherein the nickel compound and the phosphite compound are used as preliminarily mixed, or as preliminarily prepared into a complex of nickel with the phosphite compound.

11. The method according to claim 1, wherein the nickel compound and the phosphite compound are contacted with an organic aluminum in the presence of the olefin.

* * * * *